United States Patent [19]

Evers et al.

[11] 4,064,278
[45] Dec. 20, 1977

[54] FLAVORING WITH α-OXY(OXO)MERCAPTANS

[75] Inventors: William J. Evers, Red Bank; Howard H. Heinsohn Jr., Hazlet; Manfred Hugo Vock, Locust, all of N.J.

[73] Assignee: International Flavors & Fragrances Inc., New York, N.Y.

[21] Appl. No.: 774,061

[22] Filed: Mar. 3, 1977

Related U.S. Application Data

[62] Division of Ser. No. 723,535, Sept. 15, 1976, Pat. No. 4,024,289.

[51] Int. Cl.$^2$ ............................................. A23L 1/235
[52] U.S. Cl. .................................................... 426/535
[58] Field of Search .................... 426/535; 260/609 R; 260/593 R

[56] References Cited

U.S. PATENT DOCUMENTS

| | | | |
|---|---|---|---|
| 3,773,524 | 11/1973 | Katz et al. ............................. | 426/535 |
| 3,952,062 | 4/1976 | Lamparsky et al. ........ | 260/593 R X |
| 3,970,689 | 7/1976 | Stoffelsma et al. ............. | 426/535 X |
| 4,024,289 | 5/1977 | Evers et al. ........................... | 426/535 |

OTHER PUBLICATIONS

Fenaroli's Handbook of Flavor Ingredients, Edited by Furia et al., 2nd Ed., 1975, vol. 2, CRC Press Inc.: Cleveland, p. 334.

*Primary Examiner*—Joseph M. Golian
*Attorney, Agent, or Firm*—Arthur L. Liberman; Franklin D. Wolffe

[57] ABSTRACT

The fruity flavor of a foodstuff is augmented or enhanced by the use of one or more α-oxy(oxo)mercaptans selected from the group consisting of:
- 3-mercapto-4-heptanol;
- 4-mercapto-5-nonanol;
- 4-mercapto-5-nonanone;
- 3-mercapto-2,6-dimethyl-4-heptanone;
- 2-mercaptocyclododecanone-1; and
- 2-mercapto-3-pentanone These compounds augment or enhance the green, grapefruit, fruity, buchu leaf oil-like, floral, green vegetable and/or minty aromas and grapefruit-like, green, citrus, bitter, lemon, buchu leaf oil-like, blackcurrant-like, green vegetable-like, and/or cooling notes of food flavors.

4 Claims, 14 Drawing Figures

FIG.I
NMR SPECTRUM FOR EXAMPLE I-(b)
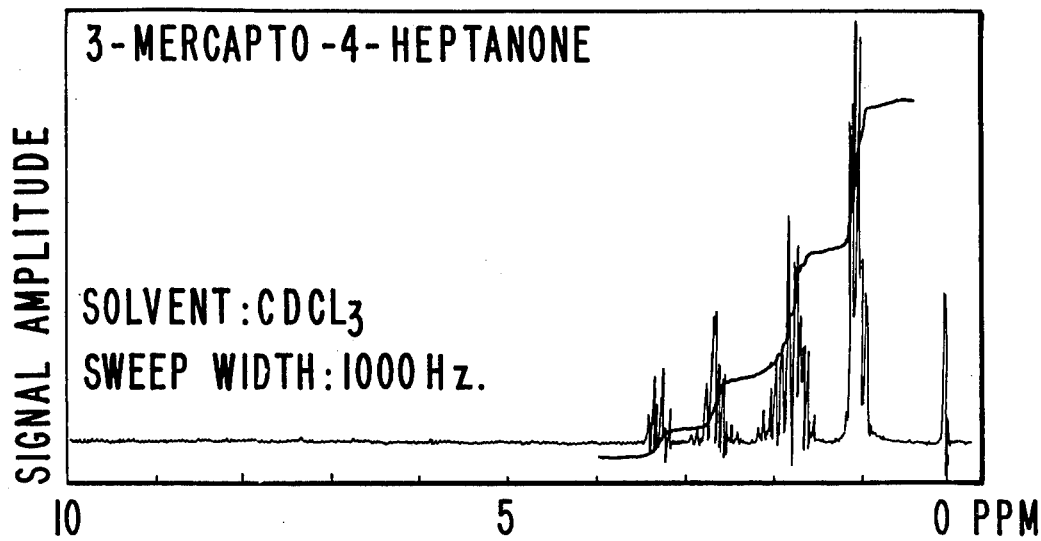
FIG.2
IR SPECTRUM FOR EXAMPLE I-(b)
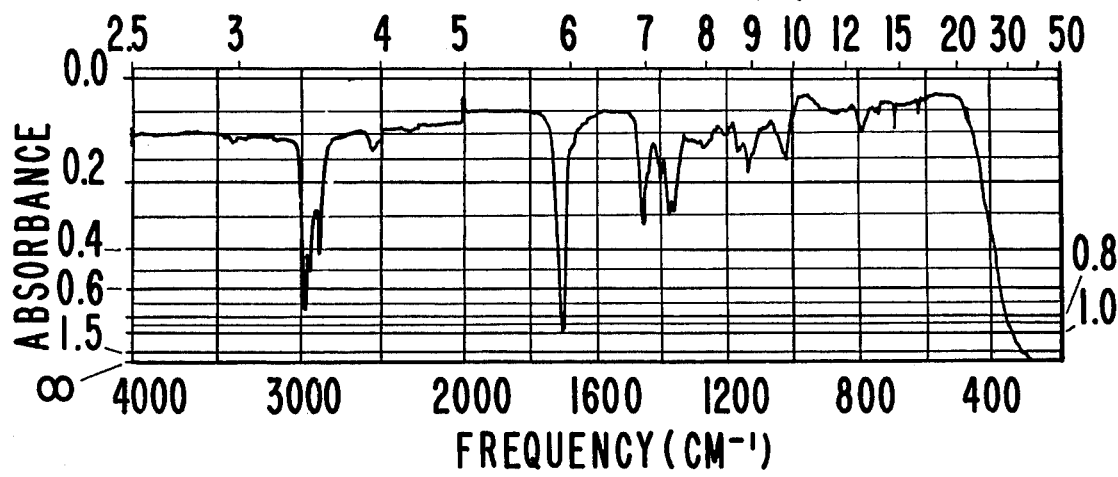

NMR SPECTRUM FOR EXAMPLE I(c)

3-MERCAPTO-4-HEPTANOL

SOLVENT: $CDCL_3$

SWEEP WIDTH: 1000 cps

IR SPECTRUM FOR EXAMPLE I(c)

FIG. 5
NMR SPECTRUM FOR EXAMPLE II (b)
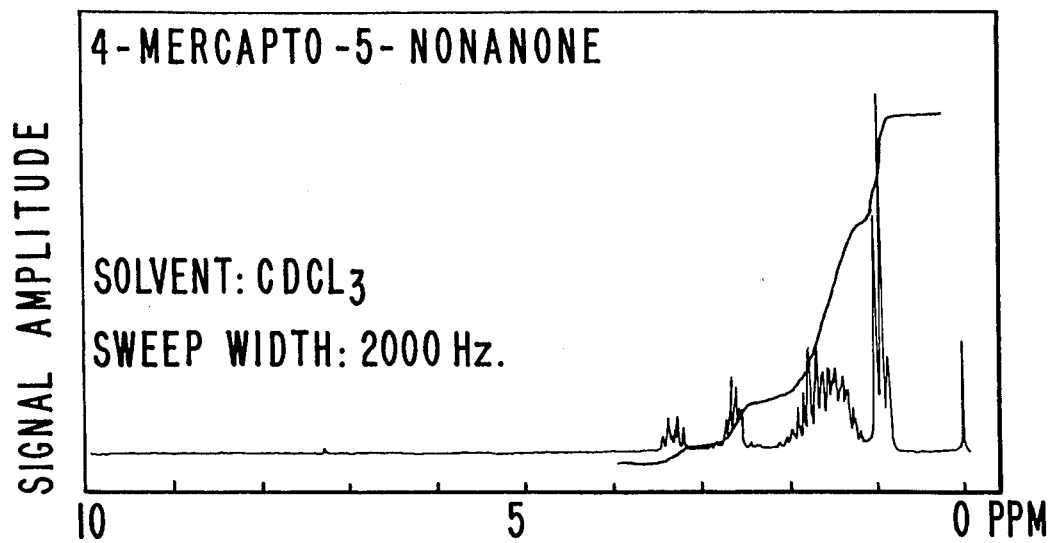
4-MERCAPTO-5-NONANONE
SOLVENT: $CDCL_3$
SWEEP WIDTH: 2000 Hz.
IR SPECTRUM FOR EXAMPLE II (c)
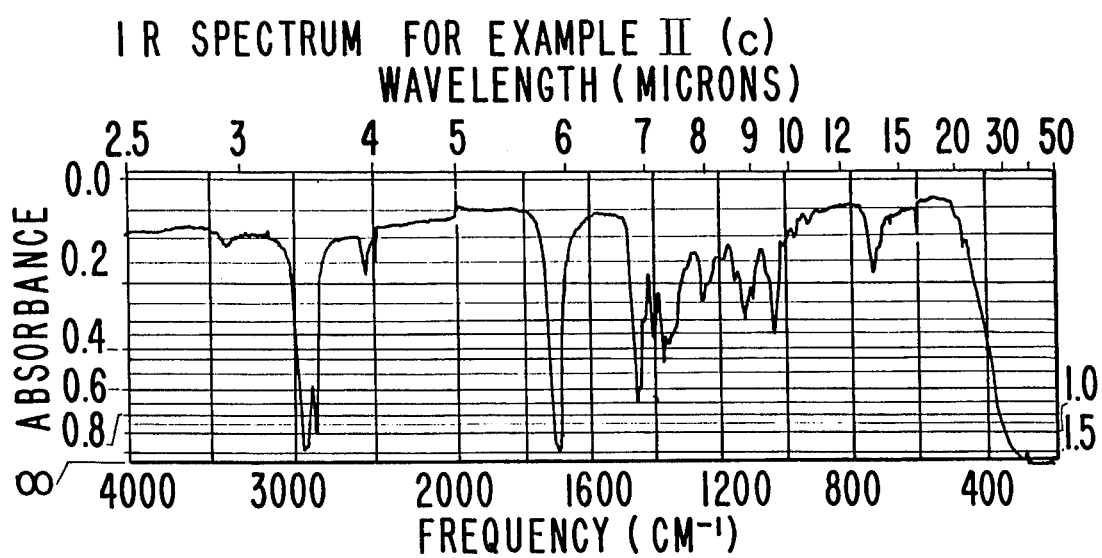
FIG. 6

NMR SPECTRUM FOR EXAMPLE III

IR SPECTRUM FOR EXAMPLE III

IR SPECTRUM FOR EXAMPLE IV

IR SPECTRUM FOR EXAMPLE V

FLAVORING WITH α-OXY(OXO)MERCAPTANS

This application is a divisional of U.S. application for Letters patent Ser. No. 723,535, filed on Sept. 15, 1976, now U.S. Pat. No. 4,024,289 issued on May 17, 1977.

BACKGROUND OF THE INVENTION

This invention relates to the augmenting or enhancing of the fruity flavor or aroma of foodstuffs. More particularly, the invention relates to the use of certain α-oxy(oxo)mercaptans to augment or enhance the fruity flavor characteristics of a foodstuff. Contemplated are processes and compositions for augmenting or enhancing the flavor of foodstuffs.

The term "augment" in its various forms is used herein to mean the supplying, modifying or imparting of a flavor or aroma characteristic, note or nuance to an otherwise bland, relatively tasteless or non-odorous substance or modifying an existing flavor or aroma characteristic where the natural flavor is deficient in some regard, or supplementing the existing flavor or aroma impression to modify its quality, character, taste or aroma.

The term "enhance" is used herein to mean the intensification of a flavor or aroma characteristic or note without the modification of the quality thereof. Thus, "enhancement" of a flavor or aroma means that the enhancement agent does not add any additional flavor note or nuance.

As used herein, the term "foodstuff" includes both solid and liquid ingestible materials which usually do, but need not, have nutritional value. Thus, foodstuffs includes soups, convenience foods, beverages, dairy products, candies, vegetables, cereals, soft drinks, snacks and the like.

As used herein, the term "medicinal products" includes both solids and liquids which are ingestible non-toxic materials which have medicinal value such as cough syrups, cough drops, aspirin and chewable medicinal tablets.

The term "chewing gum" is intended herein to be a foodstuff which is a composition which comprises a substantially water-insoluble, chewable plastic gum base such as chicle, or substitutes therefor, including jelutong, guttakay, rubber or certain comestible natural or synthetic resins or waxes. Incorporated with the gum base in admixture therewith may be plasticizers or softening agents, e.g., glycerine; and a flavoring composition which incorporates one or more of the α-oxy(oxo)-mercaptans of our invention, and, in addition, sweetening agents which may be sugars, including sucrose or dextrose and/or artificial sweeteners such as cyclamates or saccharin. Other optional ingredients may also be present.

The reproduction of fruity flavors including citrusy and blackcurrant flavors, as well as the reproduction of vegetable flavors has been the subject of a long and continuing search by those engaged in the production of foodstuffs. The shortage of foods in many parts of the world has given rise to a need for utilizing tasteless or poor-tasting sources of protein and for making such protein as palatable as possible. In addition, various techniques utilized in processing food detracts from their flavor quality or give rise to off-flavors. Convenience or "snack" foods are increasing in volume and they require flavoring. Accordingly, materials capable of closely simulating, improving or even exactly duplicating citrusy or blackcurrant or vegetable-like flavor and aroma have long been sought.

Green, grapefruit-like, fruity, buchu leaf oil-like, floral, green vegetable, and minty aromas and grapefruit-like, green, citrus, bitter, lemon, buchu leaf oil-like, blackcurrant-like, green vegetable, minty, and cooling tastes are particularly desirable for many uses in foodstuff flavors including chewing gum flavors, toothpaste flavors and medicinal product flavors.

In the past, prior to this last decade, it was the general opinion among those skilled in the art that straightchain compounds containing mercapto or —SH moieties were not desirable for use in conjunction with flavoring materials particularly for use in foodstuffs, because of their "rubbery" and "chemical" aromas. However, within the last decade, compounds containing the —SH moiety have been ascertained to be useful in flavors particularly for foodstuffs. USSR Pat. No. 345,677 teaches that para-menthane-8-thiol-3-one is useful as a synthetic blackcurrant flavoring for foodstuffs. This compound has the structure:

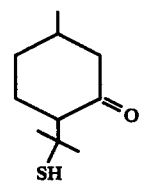

U.S. Pat. No. 3,950,429, issued on Apr. 13, 1976 discloses the use of terpenoid mercapto ketones, e.g. 6-mercapto-p-menth-8-en-2-one in straightening the floral impression of floral type perfume compositions, e.g., Lavender. Such compounds are also taught therein to be useful in augmenting, interalia, the vegetable flavors of foodstuffs.

Certain α-oxy(oxo)mercaptans are disclosed in the prior art for use as meat flavors, for example U.S. Pat. No. 3,773,524, issued on Nov. 20, 1973, discloses the use of α-ketothiols of the formula:

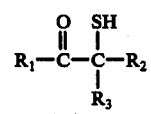

wherein $R_1$ is methyl or ethyl; and $R_2$ and $R_3$ are hydrogen, methyl or ethyl to alter the meat flavor and aroma of foodstuffs. U.S. Pat. No. 3,892,878, issued on July 1, 1975, discloses the use of certain α-hydroxy-mercaptoalkanes to alter the flavor of foodstuffs, for example, 2-mercapto-3-butanol used in meat flavors. The genus disclosed by U.S. Pat. No. 3,892,878 is as follows:

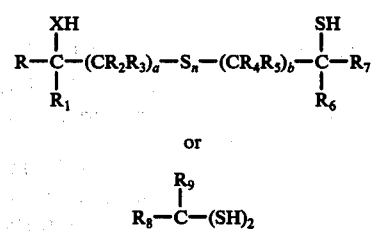

wherein X is oxygen or sulfur, $n$ is 0 or 1, $R_1$–$R_7$ are the same or different and each is hydrogen or lower alkyl of 1–4 carbon atoms, $a$ and $b$ are the same or different and each represents an integer of from 0 to 10 when n is 0 and when n is 1, a and b are the same or different and each represents an interger of from 1 to 10. 3-mercaptoheptanone-4 is disclosed per se in U.S. Pat. No. 2,888,487, issued on May 26, 1959. 3-mercapto-2,6-dimethyl-heptan-4-one is disclosed in Chem. Abstracts 6478 (d) Vol. 62, 1965 (abstract of Asinger, Diem and Schaefer, Monatsch. Chem 95 (4–5), 1335—54 (1964)). Beilstein E-IV-I discloses 2-mercapto-2,4-dimethyl-pentan-3-one at page 4039, 1-mercapto-octan-2-one at page 4040, 1-mercaptononan-2-one at 4052 and 1-mercapto-undecan-2-one at page 4060.

However, no disclosure of the prior art contains a teaching to the effect that compounds having the generic structure:

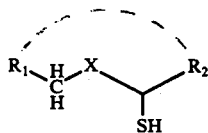

wherein X is one of:

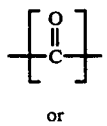

or

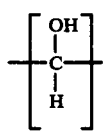

and $R_1$ and $R_2$, taken separately, are the same and are either of methyl, ethyl, 1-propyl or 2-propyl, or $R_1$ and $R_2$ taken together, is nonylene having the structure:

particularly:
3-mercapto-4-heptanol;
4-mercapto-5-nonanol;
4-mercapto-5-nonanone;
3-mercapto-2,6-dimethyl-4-heptanone;
2-mercaptocyclododecanone-1; and
2-mercapto-3-pentanone
has the ability to create intense green, grapefruit-like, fruity, buchu leaf oil-like, blackcurrant-like, floral, green vegetable and/or minty aromas and grapefruit-like, green, citrus-like, lemon-like, buchu leaf oil-like, blackcurrant-like, green vegetable-like, minty and/or cooling flavor characteristics in foodstuffs, toothpastes or medicinal products.

SUMMARY OF THE INVENTION

It has now been discovered that novel solid and liquid foodstuff, chewing gum, medicinal product and toothpaste compositions and flavoring compositions therefor having green, grapefruit-like, fruity, buchu leaf oil-like, floral, green vegetable and/or minty aromas characteristics and grapefruit-like, green, citrus, bitter, lemon, buchu leaf oil-like, blackcurrant-like, green vegetable-like, minty and/or cooling flavor characteristics may be provided by the utilization of one or more α-oxy(oxo)-mercaptans alkanes having formula:

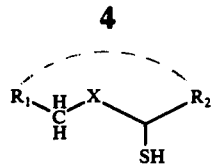

wherein X is one of:

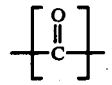

or

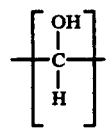

and $R_1$ and $R_2$, taken separately, are the same and are either of methyl, ethyl, 1-propyl or 2-propyl or $R_1$ and $R_2$ taken together, is nonylene having the structure:

in foodstuffs, chewing gums, toothpastes, and medicinal products.

Specifically, the α-oxy(oxo)mercaptans of our invention are as follows:
3-mercapto-4-heptanol;
4-mercapto-5-nonanol;
4-mercapto-5-nonanone;
3-mercapto-2,6-dimethyl-4-heptanone;
2-mercaptocyclododecanone-1; and
2-mercapto-3-pentanone.

Such α-oxy(oxo)mercaptans are obtained by reacting an alkanone or a cycloalkanone with $SO_2Cl_2$ to form an α-chloroalkanone or an α-chlorocycloalkanone; reacting the α-chloroalkanone or an α-chlorocycloalkanone with an alkali metal hydrosulfide to form an α-mercaptoalkanone or an α-mercaptocycloalkanone which can be used for its flavor properties; and if desired, reacting the α-mercaptoalkanone or α-mercaptocycloalkanone with a reducing agent such as an alkali metal borohydride in order to obtain an α-hydroxymercaptoalkane or an α-hydroxymercaptocycloalkane. Thus, the aforementioned reaction sequence is illustrated as follows:

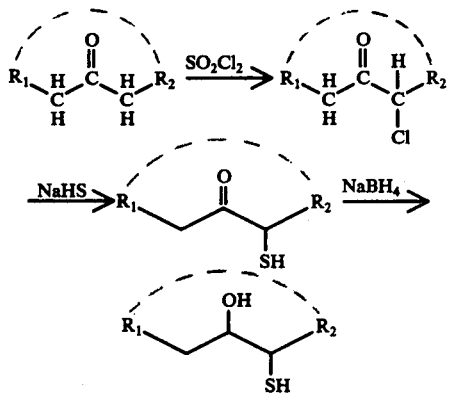

wherein $R_1$ and $R_2$ taken separately, are the same and are either methyl, ethyl, 1-propyl or 2-propyl or $R_1$ and $R_2$ taken together, is nonylene having the structure:

The reaction between the SO₂Cl₂ and ketone preferably takes place in the absence of a solvent at a temperature of between 15° and 40° C. The SO₂Cl₂ is preferably added to the ketone. At the end of the reaction, the reaction mass is worked up, the chlorinated ketone being distilled in vacuo.

The resulting chlorinated ketone is preferably reacted with sodium hydrosulfide, which is pre-prepared by reaction of hydrogen sulfide with sodium methylate in methanol. The chlorinated ketone is preferably contained in an inert solvent, e.g. in methanolic solution. Preferably the solution of chlorinated ketone is slowly added simultaneously with the addition of hydrogen sulfide to the sodium hydrosulfide solution at a temperature of between 0° and about 10° C; preferably between 0° and 4° C. At the end of the reaction, the reaction mass is concentrated, quenched with water and made alkaline. After insoluble products are extracted, the reaction mass is acidified to a pH of between 1 and 3 at which time it is extracted with a solvent such as methylene chloride. The resulting extract is then worked up using evaporation and distillation techniques whereupon the α-mercaptoalkanone or α-mercaptocycloalkanone is recovered. The resulting α-mercaptoalkanone or α-mercaptocycloalkanone is then used for its flavor properties; or it may be further reacted with a reducing agent such as sodium borohydride. The reaction with sodium borohydride takes place in an inert solvent such as anhydrous ethanol at a temperature of between 20° and 35° C. A solution in anhydrous ethanol of the α-mercaptoalkanone or α-mercaptocycloalkanone is added to the solution in anhydrous ethanol of sodium borodydride. The reaction is carried out over a period of time of between 2 and 10 hours. At the end of the reaction, the reaction mass is concentrated and is then admixed with water. The resulting mixture is acidified to a pH of between 1 and 3 and is then extracted with an inert extraction solvent such as methylene chloride. The methylene chloride extract is then dried, evaporated and the resulting α-mercaptoalkanone or α-mercaptocycloalkanone is distilled in vacuo or isolated by GLC trapping.

Specific examples of α-oxy(oxo)mercaptans produced using the aforementioned process and their flavor properties are as follows (as set forth in Table I, below):

TABLE I

| COMPOUND | STRUCTURE | AROMA |
|---|---|---|
| 3-mercapto-4-heptanol | 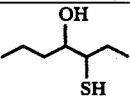 | Sulfury, green aroma with grapefruit-like nuance and sulfury, grapefruit-like, green flavor with meaty nuance at 2 ppm. |
| 4-mercapto-5-nonanone | 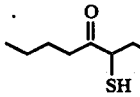 | Sulfury, fruity rubbery and grapefruit-like aroma with fruity, sulfury, citrus-and grapefruit-like flavor at 0.2 ppm. |
| 4-mercapto-5-nonanol | 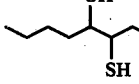 | Sulfury and fruity aroma with sulfury, rubbery, fruity, grapefruit and bitter flavor characteristics at 0.2 ppm. |
| 3-mercapto-2,6-dimethyl-4-heptanone | 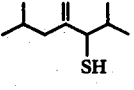 | Grapefruit-like, citrus-like, sulfury, pulegone mercaptan-like aroma with grapefruit-like lemon-like, citrus-like pulegone mercaptan-like blackcurrant-like flavor characteristics at 2 ppm. |
| 2-mercaptocyclododecanone-1 | 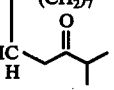 | Floral, vegetable greens-like, minty camphoraceous, sulfury aroma with vegetable greens-like, minty, cooling, sulfury flavor characteristics at 10 ppm. |
| 2-mercapto-3-pentanone | 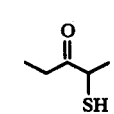 | Sweet, sulfury, meaty, allium-like aroma with sulfury, roasted, grapefruit-like, meaty flavor characteristics at 0.05 ppm. |

When the α-oxy(oxo)mercaptans of our invention are used as food flavor adjuvants or medicinal product flavor adjuvants or toothpaste flavor adjuvants or chewing gum flavor adjuvants, the nature of the co-ingredients included with each of the said α-oxy(oxo)-mercaptans in formulating the product composition will also serve to augment or enhance the organoleptic characteristics of the ultimate foodstuff, chewing gum, medicinal product or toothpaste treated therewith.

Substances suitable for use herein as co-ingredients or flavoring adjuvants are well known in the art for such use, being extensively described in the relevant literature. It is required that any such material be "ingestibly acceptable", and thus non-toxic or otherwise non-deleterious, particularly from an organoleptic standpoint whereby the ultimate flavor and/or aroma of the consumable material used does not cause the consumable material to have unacceptable aroma and taste nuances.

It is a further requirement that such material be organoleptically compatible with the foodstuff with which it is used so that the flavor and aroma nuances of such material, taken together with the flavor and aroma nuances of the foodstuff (as a whole) give rise to a harmoniously aesthically pleasing aroma and taste profile. Such materials, in general, may be characterized as flavoring adjuvants or vehicles comprising broadly, stabilizers, thickeners, surface active agents, conditioners, other flavorants and flavor intensifiers.

Stabilizer compounds include preservatives, e.g., sodium chloride, antioxidants, e.g., calcium and sodium ascorbate, ascorbic acid, butylated hydroxy-anisole (mixture of 2- and 3-tertiary-butyl-4-hydroxy-anisole), butylated hydroxy toluene (2,6-di-tertiary-butyl-4-methyl phenol), propyl gallate and the like and sequestrants, e.g., citric acid.

Thickener compounds include carriers, binders, protective colloids, suspending agents, emulsifiers and the like, e.g., agar agar, carrageenan, cellulose and cellulose derivatives such as carboxymethyl cellulose and methyl cellulose; natural and synthetic gums such as gum arabic, gum tragacanth; gelatin, proteinaceous materials, lipids; carbohydrates; starches, pectins, and emulsifiers, e.g., mono- and diglycerides of fatty acids, skim milk powder, hexoses, pentoses, disaccharides, e.g., sucrose corn syrup and the like.

Surface active agents include emulsifying agents, e.g., fatty acids such as, palmitic acid, myristic acid and the like, mono- and diglycerides of fatty acids, lecithin, defoaming and flavor-dispersing agents such as sorbitan monostearate, potassium monostearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; colorants, e.g., carminic acid, cochineal, tumeric, curcumin and the like; firming agents such as aluminum sodium sulfate, calcium chloride and calcium gluconate; texturizers, anti-caking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, formic acid, 2-hexenoic acid, benzoic acid, n-butyric acid, caproic acid, caprylic acid, cinnamic acid, isobutyric acid, isovaleric acid, alpha-methyl-butyric acid, propionic acid, valeric acid, 2-methyl-2-pentenoic acid, 2-methyl-cis-3-pentenoic acid; ketones and aldehydes, e.g., octanal, n-decanal, acetaldehyde, acetophenone, acetone, acetyl methyl carbinol, acrolein, n-butanal, crotonal, diacetyl, 2-methyl butanal, beta,betadimethyl-acrolein, methyl-n-amyl ketone, n-hexanal, 2-hexenal, isopentanal, hydrocinnamic aldehyde, cis-3-hexenal, 2-heptenal, nonyl aldehyde, citral, 4-(p-hydroxyphenyl)-2-butanone, alpha-ionone, beta-ionone, 2-methyl-3-butanone, benzaldehyde, damascone, damascenone, acetophenone, 2-heptanone, o-hydroxyacetophenone, 2-methyl-2-hepten-6-one, 2-octanone, 2-undecanone, 3-phenyl-4-pentenal, 2-phenyl-2-hexenal, 2-phenyl-2-pentenal, furfural, 5-methyl furfural, cinnamaldehyde, β-cyclohomocitral, 2-pentanone, 2-pentenal and propanal; alcohols such as 1-butanol, benzyl alcohol, 1-borneol, trans-2-buten-1-ol, ethanol, geraniol, 1-hexanol, 2-heptanol, trans-2-hexenol-1, cis-3-hexen-1-ol, 3-methyl-3-buten-1-ol, 1-pentanol, 1-penten-3-ol, p-hydroxyphenyl-2-ethanol, isoamyl alcohol, fenchyl alcohol, isofenchyl alcohol, phenyl-2-ethanol, α-terpineol, cis-terpineol hydrate, eugenol, linalool, 2-heptanol, acetoin; esters such as butyl acetate, ethyl acetate, ethyl acetoacetate, ethyl benzoate, ethyl butyrate, ethyl caprate, ethyl caproate, ethyl caprylate, ethyl cinnamate, ethyl crotonate, ethyl formate, ethyl isobutyrate, ethyl isovalerate, ethyl laurate, ethyl myristate, ethyl α-methylbutyrate, ethyl propionate, ethyl salicylate, trans-2-hexenyl acetate, hexyl acetate, 2-hexenyl butyrate, hexyl butyrate, isoamyl acetate, isopropyl butyrate, dimethylanthranilate, methyl acetate, methyl butyrate, methyl caproate, methyl isobutyrate, α-methylphenylglycidate, ethyl succinate, isobutyl cinnamate, cinnamyl formate, methyl cinnamate and terpinenyl acetate; hydrocarbons such as dimethyl naphthalene, dodecane, methyl diphenyl, methyl naphthalene, myrcene, cadinene, limonene, naphthalene, octadecane, tetradecane, tetramethyl naphthalene, tridecane, trimethyl naphthalene, undecane, caryophyllene, 1-phellandrene, p-cymene, 1-α-pinene; pyrazines such as 2,3-dimethylpyrazine, 2,5-dimethylpyrazine, 2,6-dimethylpyrazine, 3-ethyl-2,5-dimethylpyrazine, 2-ethyl-3,5,6-trimethylpyrazine, 3-isoamyl-2,5-dimethylpyrazine, 5-isoamyl-2,3-dimethylpyrazine, 2-isoamyl-3,5,6-trimethylpyrazine, isopropyl dimethylpyrazine, α-methyl-3-ethylpyrazine, tetramethylpyrazine, trimethylpyrazine; essential oils, such as jasmine absolute, cassia oil, cinnamon bark oil, rose absolute, orris absolute, lemon essential oil, orange essential oil, grapefruit essential oil, Bulgarian rose, yara yara and vanilla; lactones such as gammanonalactone; sulfides, e.g., methyl sulfide and other materials such as maltol, and acetals (e.g., 1,1-diethoxyethane, 1,1-dimethoxyethane and dimethoxymethane).

The specific flavoring adjuvants selected for use may be either solid or liquid depending upon the desired physical form of the ultimate product, i.e., foodstuff, whether simulated or natural, and should, in any event, (i) be organoleptically compatible with the α-oxy(oxo)-mercaptans of our invention by not covering or spoiling the organoleptic properties (aroma and/or taste) thereof; (ii) be non-reactive with the α-oxy(oxo)mercaptans of our invention; and (iii) be capable of providing an environment in which the α-oxy(oxo)mercaptans can be dispersed or admixed to provide a homogeneous medium. In addition, selection of one or more flavoring adjuvants, as well as the quantities thereof will depend upon the precise organoleptic character desired in the finished product. Thus, in the case of flavoring compositions, ingredient selection will vary in accordance with the foodstuff, chewing gum, medicinal product or toothpaste to which the flavor and/or aroma are to be imparted, modified, augmented or enhanced. In contradistinction, in the preparation of solid products, e.g., simulated foodstuffs, ingredients capable of providing normally solid compositions should be selected such as various cellulose derivatives.

As will be appreciated by those skilled in the art, the amount of α-oxy(oxo)mercaptans employed in a particular instance can vary over a relatively wide range, depending upon the desired organoleptic effects to be achieved. Thus, correspondingly, greater amounts would be necessary in those instances wherein the ultimate food composition to be flavored is relatively bland to the taste, whereas relatively minor quantitites may suffice for purposes of enhancing the composition merely deficient in natural flavor or aroma. The primary requirement is that the amount selected be effective, i.e., sufficient to augment or enhance the organoleptic characteristics of the parent composition, whether foodstuff per se, chewing gum per se, medicinal product per se, toothpaste per se, or flavoring composition.

The use of insufficient quantities of α-oxy(oxo)mercaptans will, of course, substantially vitiate any possibility of obtaining the desired results while excess quantities prove needlessly costly and, in extreme cases, may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, chewing gum compositions, medicinal product compositions and toothpaste compositions, it is found that quantities of α-oxy(oxo)mercaptans ranging from a small but effective amount, e.g., 0.02 parts per million (ppm) up to about 50 parts per million (ppm) based on total composition are suitable. Concentrations in excess of the maximum quantity stated are not normally recommended, since they fail to provide commensurate enhancement of organoleptic properties. In those instances, where the α-oxy(oxo)mercaptans is added to the foodstuff as an integral component of a flavoring composition, it is, of course, essential that the total quantity of flavoring composition employed be sufficient to yield an effective α-oxy(oxo)mercaptans concentration in the foodstuff product.

Food flavoring compositions prepared in accordance with the present invention preferably contain the α-oxy(oxo)mercaptans in concentrations ranging from about 0.05% up to about 5% by weight based on the total weight of the said flavoring composition.

The composition described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the α-oxy(oxo)mercaptans of our invention with, for example, gum arabic, gum tragacanth, carrageenan and the like, and thereafter spray-drying the resultant mixture whereby to obtain the particulate solid product. Pre-prepared flavor mixes in powder form e.g., a fruit-flavored powder mixes are obtained by mixing the dried solid components, e.g., starch, sugar and the like and the α-oxy(oxo)mercaptans in a dry blender until the requisite degree of uniformity is achieved.

It is presently preferred to combine with the α-oxy(oxo)mercaptans of our invention, the following adjuvants:
Bergamot oil;
Citral;
Amyl alcohol;
Ethyl acetate;
5-phenyl-4-pentenal;
5-phenyl-2-pentenal;
n-Octanal;
n-Decanal;
Limonene;
Geraniol;
Cadinene;
Dimethylanthranilate;
Vanillin;
Amyl butyrate;
2-(n-pentyl)-thiazole;
2-(i-butyl)-thiazole;
2-(i-propyl)-thiazole;
2-(n-propyl)-thiazole;
The dimethyl acetal of 2-phenyl-4-pentenal;
Methional;
4-Methylthiobutanal;
2-Ethyl-3-acetyl pyrazine;
Tetramethyl pyrazine;
2-Methyl pyrazine;
2-Trans hexenal;
Maltol;
2-Phenyl-4-pentenal;
2-Phenyl-4-pentenal dimethyl acetal; and
2-Phenyl-4-pentenal diethyl acetal.

The following examples are intended to illustrate the instant invention. It will be understood that these examples are illustrative and that the invention is to be considered restricted thereto only as indicated in the appended claims.

All parts and percentages given herein are by weight unless otherwise specified.

EXAMPLE I

Part (A)

PREPARATION OF 3-CHLORO-4-HEPTANONE

Reaction:

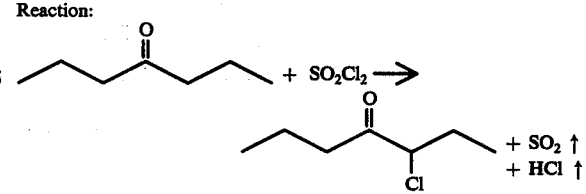

Into a 3000 ml, three-necked, round-bottom flask, equipped with mechanical stirrer, 500 ml addition funnel, Y-tube, pot thermometer and gas outlet tube with rubber tubing leading over a stirring solution of 10% sodium hydroxide is added 1000 g 4-heptanone. Addition of 434 g of SO$_2$Cl$_2$ drop-wise into the 4-heptanone is commenced while maintaining the pot temperature in the range of 22°-34° C and is continued over a period of two hours. A water aspirator vacuum is applied to the reaction mass in order to pull the acidic gases; sulfur dioxide and hydrogen chloride, over the NaOH solution.

The reaction mass is periodically sampled using GLC analysis until such time as about 25% mono-chlorinated ketone product is found to be present.

While maintaining the reaction mass at 15° C, 1000 ml saturated sodium chloride is added to the mixture, and the mixture is then stirred for a period of 10 minutes.

The reaction mass is then transferred to a 5-liter separatory funnel and shaken well, whereupon the organic and aqueous phases separate. The lower aqueous phase (approximately 1000 ml) has a pH of about 1. The upper organic phase is washed with 700 ml saturated sodium bicarbonate solution to a pH of 6–7. The organic phase is then dried over 50 grams anhydrous sodium sulfate and filtered yielding a yellow oil weighing 1063 grams. The organic layer is determined to contain 24.94% chlorinated ketone and 68.12% original ketone starting material. This material is then vacuum distilled by first adding it to a 2000 ml, three-necked, round-bottom flask equipped with a 2.5 × 60 cm vacuum jacketed column packed with 6 mm Raschig Rings, and equipped with an automatic reflux head, a pot thermometer, a heating mantle, a vacuum pump and a dry-ice trap. Fractionation data is as follows:

| Vacuum (mmHg) | Pot Temp. | Vapor Temp. | Weight of Fraction | Cut. No. | Reflux Ratio |
|---|---|---|---|---|---|
| 62 | 80 | 71 | 51.0 g | 1 | 60:40 |
| 62 | 81.5 | 71 | 149.0 g | 2 | 40:60 |
| 58 | 82.5 | 70 | 157.5 g | 3 | 30:70 |
| 59 | 89.5 | 70 | 175.0 g | 4 | 30:70 |
| 59 | 96 | 75 | 110 g | 5 | 30:70 |
| 59 | 100 | 80 | 24.5 g | 6 | 50:50 |
| 58 | 101 | 90 | 16.0 g | 7 | 50:50 |
| 58 | 102 | 94 | 37.5 g | 8 | 30:70 |
| 55 | 103 | 94 | 144.5 g | 9 | 30:70 |
| 54 | 110 | 95 | 85.0 g | 10 | 30:70 |
| 54 | 119 | 102 | 28.0 g | 11 | 30:70 |
| 15 | 140 | 80 | 45.0 g | 12 | 30:70 |

GLC analysis on each of cuts 5–12 (conditions 8 feet × ¼ inch SE-30 column) yields the following information:

Into a 50 ml, three-necked, round-botton flask, equipped with magnetic stirrer, pot thermometer, 6 inch distillation column with gas outlet at top attached to rubber tubing leading above stirring solution of 10% sodium hydroxide solution, gas inlet tube (for hydrogen sulfide bubbling), gas bubbler, empty trap between hydrogen sulfide cylinder and bubbler, hydrogen sulfide cylinder, and isopropanol/dry-ice bath, is added a solution of 1.62 g sodium methoxide dissolved in 13.5 ml anhydrous methanol. The sodium methoxide solution is cooled to −10° C and the hydrogen sulfide bubbling is commenced below the surface of the sodium methoxide solution. The reaction is maintained at a temperature of −5° to −10° C, while continuing the hydrogen sulfide bubbling and stirring the reaction mass for a period of 1½ hours. At this point 5 ml of the cold sodium hydrosulfide solution is tranferred to a 25 ml Erlenmeyer flask equipped with magnetic stirrer, dry nitrogen flow, pot thermometer and isopropanol/dry-ice bath. At −4° to 0° C, 0.75 g (0.005 moles) of 3-chloro-4-heptanone is added dropwise over one minute using a pipette. After all of the chlorinated ketone is added, a heavy solid precipitate forms which is stirred at 0° C for 15 minutes, then allowed to warm to 23° C over an additional 50 minute time period. About 4 ml of 10% sodium hydroxide solution is then added to the reaction mass while stirring under a nitrogen blanket. Unreacted chloro ketone is extracted with 7 ml of methylene chloride and separated. The basic aqueous phase is acidified to a pH of 2 with 10% aqueous hydrochloric acid. The oil out is extracted twice with 10 ml methylene chloride. The methylene chloride extracts are combined, washed with saturated sodium chloride solution, dried and concen-

| Cut. No. | Percent low Boilers | Percent 4-Heptanone | Percent 3-Cl 4-Heptanone | Percent High Boiler (A) | Percent High Boiler (B) | Percent High Boiler (C) | Percent High Boiler (D) |
|---|---|---|---|---|---|---|---|
| 5 | 0.09 | 96.15 | 2.97 | — | — | — | — |
| 6 | | | | | | | |
| 7 | | 50% | 50% | | | | |
| 8 | — | 9.28 | 87.09 | 2.43 | 0.57 | — | — |
| 9 | — | trace | 95.78 | 3.22 | 1.00 | — | — |
| 10 | — | — | 91.38 | 4.89 | 3.34 | 0.21 | — |
| 11 | — | — | 69.14 | 7.27 | 19.88 | 3.71 | — |
| 12 | — | — | 8.32 | 2.07 | 49.28 | 39.69 | 0.47 |

Cuts 8, 9 and 10 are blended (weight 266.5 gms) and are analyzed by GLC as follows:

| 0.95% | 4-heptanone |
|---|---|
| 93.89% | 3-chloro-4-heptanone |
| 3.60% | high boiler A |
| 1.57% | high boiler B |

Part (B)

PREPARATION OF 3-MERCAPTO-4-HEPTANONE

Reaction:

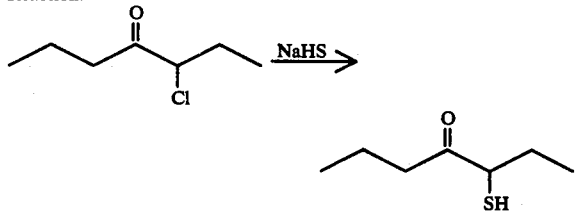

trated to yield 0.55 gms of product. GLC, IR and NMR analyses of trapped product yield the information that the product is 3-mercapto-4-heptanone.

The NMR spectrum is set forth in FIG. 1. The infrared spectrum is set forth in FIG. 2.

The NMR analysis is as follows:

| | | |
|---|---|---|
| 1.04 ppm (t) | CH$_3$—C—C—C— with O double bond | 6 H |
| 1.00 (t) | CH$_3$—C—C—C— with O double bond and S— | |
| 2.20–1.40 (m) | —CH$_2$— / —SH | 5 H |
| 2.62 (m) | —CH$_2$—C— with O double bond | 2 H |
| 3.26 (m) | O=C—CH—S— | 1 H |

The infra-red analysis is as follows:
1130 cm$^{-1}$, 1360, 1370, 1400, 1450, 1705, 2540, 2870, 2930, 2960.

Part (C)

PREPARATION OF 3-MERCAPTO-4-HEPTANOL

Reaction:

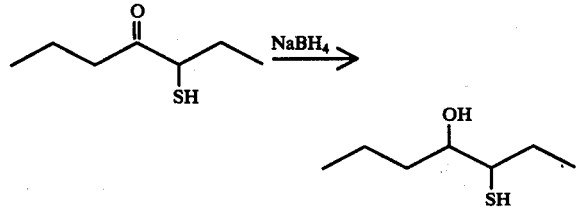

Into a 25 ml, round-bottom flask, equipped with magnetic stirrer, nitrogen inlet tube, gas outlet tube, dry-ice-/acetone bath and reflux condenser is added 2.5 ml of a 95% ethanolic solution containing 0.06 gms of sodium borohydride (0.0015 moles). While maintaining the reaction mass at a temperature of between 25° and 35° C over a period of about 5 minutes, 0.44 gms (0.003 moles) of 3-mercapto-4-heptanone in 95% ethanol (2.5 ml) is added to the sodium borohydride solution. During this time, the reaction mass is stirred under a blanket of dry nitrogen.

The reaction mass is then continued to be stirred for a period of three hours at which time the reaction mixture is concentrated on a rotary evaporator using water aspirator vacuum to 3 ml of a thick slurry. To the slurry is added 10 ml water with stirring, and the solid then dissolves. The aqueous solution is then acidified to a pH of 6 with 4% aqueous hydrochloric acid, at which time the reaction mass exists in two phases; an aqueous phase and an organic phase. The organic phase is extracted with two 10 ml portions of methylene chloride. The extracts are combined, dried over anhydrous sodium sulfate, gravity filtered and concentrated on a rotary evaporator to yield a yellow oil weighing 0.3 gms. GLC analysis (conditions: 8 feet × ¼ inch SE-30 column) indicates 96.3% 3-mercapto-4-heptanol. NMR and IR analyses of trapped product confirm the structure of this material.

The NMR spectrum is set forth in FIG. 3. The IR spectrum is set forth in FIG. 4.

The NMR analysis is as follows:

| 1.28–0.92 | CH$_3$— + —SH | 7 H |
| 1.48 (m) | —CH$_2$— | 6 H |
| 1.96 (s) | OH | 1 H |
| 2.74 (m) | HC—S— | 1 H |
| 3.58 (m) | HC—O— | 1 H |

The infra-red analysis is as follows:
1000 cm$^{-1}$, 1050, 1070, 1110, 1130, 1280, 1370, 1450, 2540, 2860, 2920, 2950, 3400.

EXAMPLE II

Part (A)

PREPARATION OF 4-CHLORO-5-NONANONE

Reaction:

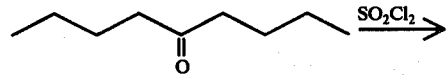

-continued

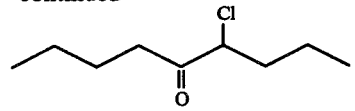

Into a 250 ml, three-necked, round-bottom flask, equipped with magnetic stirrer, six inch Vigreux column (with gas outlet to vacuum), cold water bath, pot thermometer, water aspirator vacuum and 50 ml addition funnel are placed 99 gms of 5-nonanone. 31.6 gms (18.7 ml; 0.234 moles) of SO$_2$Cl$_2$ are added dropwise from the addition funnel over a period of one hour while maintaining the reaction mass at a temperature of between 24° and 27° C. Water aspirator vacuum is applied to the reaction flask while stirring, in order to remove acidic gases.

The reaction mass is then warmed to 30° C and evaporated on a rotary evaporator.

The weight of crude material is 108 gms and contains 73% nonanone, and 21.4% of 4-chloro-5-nonanone.

A 250 ml, three-necked, round-bottom flask, equipped with magnetic stirrer, 1.3 × 30 cm distillation column, packed with 6 mm Raschig Rings, reflux head, heating mantle, pot thermometer, vacuum pump, and dry-ice/isopropanol trap is used in order to distill the chlorononanone from the reaction mass The 4-chloro-5-nonanone is then distilled at a temperature from 105°–108° C and a pressure of 22.5–23 mm Hg yielding 16.7 gms of product. This material is used in Part (B), supra.

Part (B)

PREPARATION OF 4-MERCAPTO-5-NONANONE

Reaction:

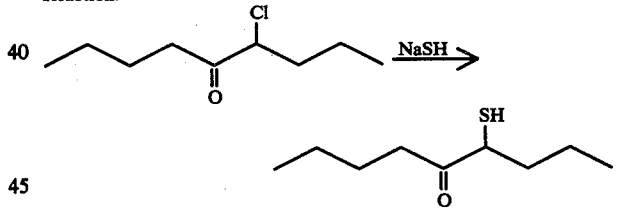

Into a 250 ml, three-necked, round-bottom flask equipped with magnetic stirrer, pot thermometer, six inch distillation column with gas oulet at top with rubber tubing leading above a 10% sodium hydroxide solution, a gas inlet tube (sub-surface), a gas bubbler, an empty trap between the hydrogen sulfide cylinder and bubbler, a dry-ice/isopropanol bath, and a 10 ml addition funnel, the following materials are added with stirring at 25° to 40° C:

40 ml anhydrous methanol;
4.88 gms sodium methylate (0.0903 moles).

While maintaining the temperature of the reaction mass at between −5° and −15° C addition of hydrogen sulfide is commenced, bubbling the hydrogen sulfide below the surface of the reaction mass. The hydrogen sulfide bubbling is continued for a period of two hours at which time it is ceased and addition of the 4-chloro-5-nonanone produced in Example I (A), supra, is commenced. The 4-chloro-5-nonanone is added over a period of 10 minutes while maintaining the reaction mass at a temperature of between −9° and −10° C.

The reaction mass is then stirred at 0° C, while hydrogen sulfide addition continues for a period of 1 hour.

The reaction mass is then concentrated to a yellow solution containing a white solid precipitate on a rotary evaporator to 15 ml. 35 ml water is then added with stirring followed by 35 gms of a 10% aqueous sodium hydroxide solution. Stirring is continued for a period of 10 minutes while maintaining the resulting mixture at a temperature of between 24° and 27° C. The resulting basic aqueous solution is then extracted with two portions (35 ml each) of methylene chloride and the extracts are combined, dried, and concentrated yielding an oil weighing 1.1 gms. The aqueous solution is then acidified to a pH of 1–2 using 42 ml, 10% hydrochloric acid while being cooled to 25°–30° C. It is then extracted with four 25 ml portions of methylene chloride and the extracts are combined, and washed with two 30 ml portions of saturated sodium chloride. The methylene chloride extracts are dried over anhydrous sodium sulfate, gravity filtered, and concentrated on a rotary evaporator to yield a light yellow oil having a weight of 6.6 gms.

GLC, IR and NMR analyses yield the information that this light yellow oil contains 94.36% 4-mercapto-5-nonanone.

The NMR spectrum is set forth in FIG. 5. The infra-red spectrum is set forth in FIG. 6.

The NMR analysis is as follows:

| | | |
|---|---|---|
| 0.94 ppm (t) | CH$_3$—CH$_2$— | 6 H |
| 1.72 (d) | SH | |
| 2.04–1.18 (m) | —CH$_2$— | 9 H |
| 2.60 (m) | —CH$_2$—$\overset{O}{\overset{\|}{C}}$— | 2 H |
| 3.32 (m) | —$\overset{O}{\overset{\|}{C}}$—HC—S— | 1 H |

The infra-red analysis is as follows:
1040 cm$^{-1}$, 1150, 1355, 1375, 1400, 1430, 1460, 1700, 2250, 2870, 2960.

Part (C)

PREPARATION OF 4-MERCAPTO-5-NONANOL

Reaction:

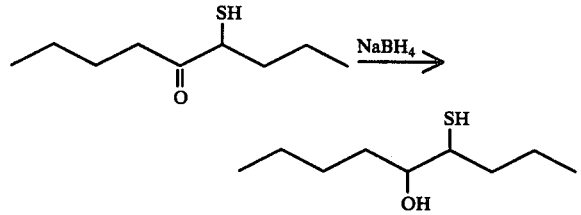

Into a 25 ml, round-bottom, three-necked flask, equipped with magnetic stirrer, pot thermometer, reflux condenser and nitrogen inlet tube is added 0.066 gms of sodium borohydride dissolved in 3 ml ethyl alcohol. Under nitrogen, 0.554 gms of 4-mercapto-5-nonanone produced according to the process of Example II (B) is dissolved in 2.5 ml of anhydrous ethanol and the resulting solution is added by pipette to the sodium borohydride solution over a period of four minutes at 23° to 34° C. The reaction mass then cools to 25° C and is maintained at a temperature of from 23°–25° C for a period of one hour.

GLC analysis indicates that 74.4% of 4-mercapto-5-nonanol is formed at this point. An additional 0.033 gms of sodium borohydride in 1.5 ml ethyl alcohol is added and the reaction mass is stirred for 3 hours.

The reaction mass is concentrated on a rotary evaporator (using water aspirator vacuum) to a volume of about 3 ml and a thick slurry is obtained. 7 ml of water is then added and the solid dissolves yielding a turbid and oily liquid having a pH of about 10. The reaction mass is then neutralized to a pH of between four and five with 35 drops of a 10% aqueous HCl solution. The reaction mass is then extracted with two 10 ml portions of methylene chloride and the extracts are combined, washed with 3 ml water and then dried over anhydrous soidum sulfate. The methylene chloride solution is gravity filtered and evaporated on a rotary evaporator to yield 0.44 gms of a pale yellow oil. GLC analysis indicates that the resulting material is 98.2% 4-mercapto-5-nonanol.

IR and NMR analyses confirm the structure. The NMR spectrum is set forth in FIG. 7. The infra-red spectrum is set forth in FIG. 8.

The NMR analysis is as follows:

| | | |
|---|---|---|
| 0.94 ppm (diffuse triplet) | CH$_3$—CH$_2$— | 6 H |
| 1.20 (d) | SH | 1 H |
| 1.46 (broad) | —CH$_2$— | 10 H |
| 2.06 | OH | 1 H |
| 2.80 (m) | HC—S— | 1 H |
| 3.54 (m) | HC—O— | 1 H |

The infra-red analysis is as follows:
1020 cm$^{-1}$, 1115, 1370, 1460, 2550, 2870, 2920, 2950, 3420.

EXAMPLE III

Part (A)

PREPARATION OF 2,6-DIMETHYL-3-CHLOROHEPTANONE-4

Reaction:

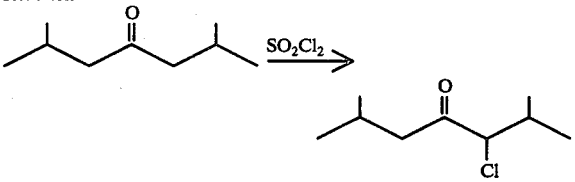

Into a one-liter, three-necked, round-bottom flask, equipped with "Y-tube", pot thermometer, mechanical stirrer, 125 ml addition funnel, gas outlet tube, cold water bath and water aspirator vacuum is placed 356 gms of 2,6-dimethyl-4-heptanone. 67.5 gms (0.5 moles) of SO$_2$Cl$_2$ is then added to the ketone, with stirring, while maintaining the reaction mass at a temperature of between 23° and 35° C, over a period of one hour.

At the end of the addition of the SO$_2$Cl$_2$, most of the acidic gases are removed using water aspirator vacuum. The reaction mass is then transferred to a one-neck, one-liter, round-bottom flask and evaporated on a rotary evaporator using water aspirator vacuum yielding a crude product weighing 371 gms. This crude material is then transferred to a 500 ml, three-necked, round-bottom flask, equipped with a 2.0 × 30 cm column packed with ⅛ inch helices, reflux head, magnetic stirrer, heating mantle, and vacuum pump. The 2,6-dimethyl-3-chloroheptanone-4 is then distilled at a vapor temperature of 106°–107° C and a pressure of 45–46 mm Hg, yielding 37 gms of product.

Mass Spectral, NMR and IR analyses confirm that the resulting material is 2,6-dimethyl-3-chloro-heptanone-4. This material is used in the process of Example III (B), infra.

Part (B)

PREPARATION OF 2,6-DIMETHYL-3-MERCAPTOHEPTANONE-4

Reaction:

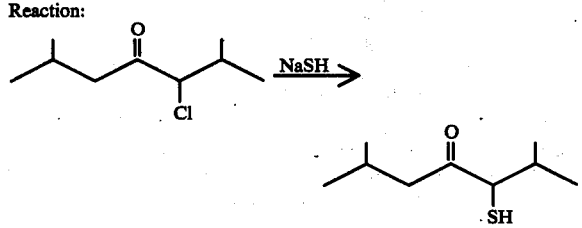

Into a 250 ml, three-necked, round bottom flask, equipped with magnetic stirrer, pot thermometer, six inch Vigreux distillation column, with gas outlet at top leading over 200 ml of a 10% aqueous sodium hydroxide solution, a hydrogen sulfide gas inlet tube (sub-surface), a "Y-tube", a 50 ml addition funnel, gas bubbler, a dry-ice/isopropyl alcohol bath, and a cold water bath, is added 11.6 gms of sodium methylate dissolved in 90 ml anhydrous methanol. While maintaining the temperature at between −5° and −10° C, hydrogen sulfide bubbling is commenced and continued over a period of two hours. At the end of the two hour period, while continuing hydrogen sulfide bubbling, 2,6-dimethyl-3-chloro-heptanone-4 (18.2 gms) is added to the solution while maintaining the reaction temperature at between −5° and −9° C. The addition of the chloro ketone takes place over a period of 13 minutes. Hydrogen sulfide bubbling is continued for a period of four hours while maintaining the reaction mass at temperatures of between 0° and 26° C (25°–26° C for the last 1.5 hours).

The resulting reaction mass is then concentrated to a yellow solution containing a white solid (25 ml volume) on a rotary evaporator to which is applied a water aspirator vacuum. 85 ml of distilled water is added to the reaction product with stirring while maintaining the reaction mass at 25° C whereupon the solid dissolves yielding a turbid yellow solution. 85 gms of a 10% aqueous sodium hydroxide solution is then added to the reaction mass while maintaining same at 25°–28° C (pH = 10–11). The reaction mass is then extracted with two 70 ml portions of methylene chloride and the methylene chloride extracts are combined, dried and concentrated yielding 1.7 gms of an oil.

The basic aqueous solution is then acidified with 115 ml aqueous 10% hydrochloric acid to a pH of between one and two. The resulting acidified solution is extracted with four 50 ml portions of methylene chloride and the methylene chloride extracts are combined and washed with two 35 ml portions of saturated sodium chloride and dried over anhydrous sodium sulfate. The resulting material is gravity filtered and concentrated on a rotary evaporator to yield 15.5 gms of a pale yellow liquid containing 96.1% 2,6-dimethyl-3-mercaptoheptanone-4 as confirmed by Mass Spectral, NMR and IR analyses. The reaction product is trapped using an 8 feet × ¼ inch SE-30 GLC column, programmed at 130° C, at 7.5° C/minute.

The NMR Spectrum is set forth in FIG. 9. The IR Spectrum is set forth in FIG. 10.

The NMR analysis is as follows:

| | | |
|---|---|---|
| 0.98 | methyl protons | 12 H |
| 1.62 | —SH | 1 H |
| 2.12 | methine protons | 2 H |
| 2.46 | $CH_2-\overset{\overset{O}{\|}}{C}-$ | 2 H |
| 3.10 | HC—S | 1 H |

The infra-red analysis is as follows:
1040 cm$^{-1}$, 1365, 1375, 1465, 1705, 2550, 2870, 2920, 2960.

13.27 gms of material produced according to this example is placed in a 25 ml, three-necked, round bottom flask, equipped with a 1.6 × 15 cm Vigreux column, magnetic stirrer, reflux head, heating mantle and vacuum pump. The material is distilled at a vapor temperature of 77.5°–78° C and a vacuum of 6 mm Hg, and the thus-distilled material has the same physical properties as set forth above, for 2,6-dimethyl-3-mercapto-heptanone-4.

EXAMPLE IV

Part (A)

PREPARATION OF 2-CHLORO-CYCLODODECANONE

Reaction:

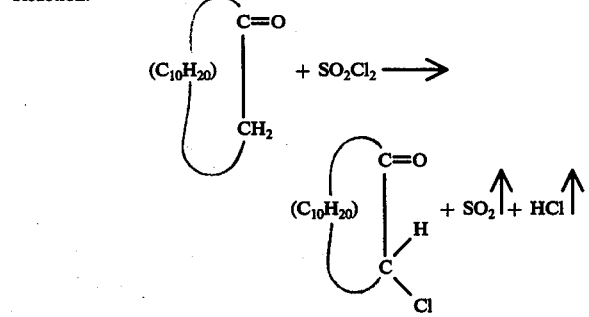

Into a 1000 ml three-necked, round-bottom flask, equipped with "Y-tube", mechanical stirrer, thermometer, 125 ml addition funnel, vacuum adapter to water aspirator and water bath is placed a solution of 100 g of cyclododecanone in 100 ml anhydrous benzene. The cyclododecanone is dissolved in the benzene with stirring at 25° C. and the solution cools by itself as the solution occurs, to 10° C. The solution then is allowed to warm up to 26° C, at which point dropwise addition of $SO_2Cl_2$ is commenced with stirring. Addition of $SO_2Cl_2$ continues for a period of 1 hour at 26°–33° C, during which time acidic gases are removed using a water aspirator vacuum. At the end of the addition, stirring is continued for another one hour period. The reaction mass is then transferred to a 1000 ml, one-neck, round-bottom flask and concentrated on a rotary evaporator during which time the benzene solvent is trapped in a dry-ice/acetone trap. GLC analysis on an 8 feet × ¼ inch SE-30 column yields the information that the reaction product contains approximately 24% chlorinated ketone. The reaction product (117 g) is introduced into a 250 ml, three-necked round-bottom flask, equipped with a 2.0 × 30 cm distillation column, packed with ⅛ inch helices, reflux head, magnetic stirrer, heating mantle, high vacuum pump and dry-ice trap. Unreacted cyclododecanone (72.5 g) is recovered, distilling at 95°-113° C vapor temperature and 0.6-1.2 mm Hg pressure. The residue (30.3 g) is transferred to a 100 ml, three-necked, round bottom flask, equipped with a 1.3 × 17 cm unpacked distillation column. Fractionation proceeds as follows:

| Pressure | Pot Temperature | Vapor Temperature | Weight of Fraction | Analysis of Fraction |
| --- | --- | --- | --- | --- |
| 0.4 mm Hg | 123.5° C | 105° C | 2.23 Ag | 39.2% starting ketone and 60.8% chlorinated ketone |
| 0.5 mm Hg | 128° C | 115° C | 7.27 g | 21.8% starting ketone and 78.0% chlorinated ketone |
| 0.5 mm Hg | 140° C | 112° C | 13.53 g | 4.5% starting ketone and 94% chlorinated ketone |
| 0.5 mm Hg | 195° C | 120° C | 1.36 g | 1.5 starting ketone and 62.8% chlorinated ketone |

Mass spectral, NMR and IR analyses of GLC trapped product (8 feet × ¼ inch SE-30 column) confirm the resulting material is 2-chloro-cyclododecanone. The distilled product (94% chlorinated ketone) is used in the process of Example IV (B), infra.

Part (B)

PREPARATION OF 2-MERCAPTO-CYCLODODECANONE

Reaction:

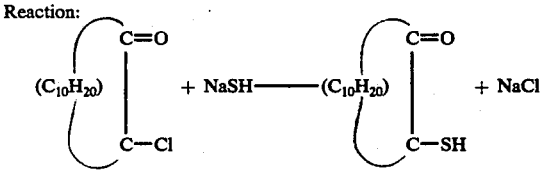

Into a 250 ml, three-necked, round-bottom flask, equipped with magnetic stirrer, pot thermometer, six inch distillation column with gas outlet at top attached to rubber tubing leading above a stirring 10% NaOH solution, gas inlet tube (for hydrogen sulfide bubbling), gas bubbler (Primol ®), empty tray between hydrogen sulfide cylinder and bubbler, hydrogen sulfide cylinder, isopropanol/dry-ice bath and 50 ml addition funnel is added a solution of 4.65 g of sodium methoxide dissolved in 45 ml anhydrous methanol. The sodium methoxide solution is cooled to −10° C, at which point hydrogen sulfide bubbling is commenced below the surface of the sodium methoxide solution. The reaction is maintained at a temperature of −5° to −10° C, during which time the hydrogen sulfide bubbling proceeds while stirring the reaction mass for a period of 1½ hours. At this point in time, 90 ml anhydrous methanol is used to dissolve completely the chlorinated ketone starting material at room temperature. While maintaining the reaction mass at 0°-4° C, the methanolic solution of chlorinated ketone is added dropwise during simultaneous slow flow of hydrogen sulfide. After all the chlorinated ketone solution is added (after another ½ hour) a heavy solid precipitate forms which is stirred under hydrogen sulfide flow. At the end of an additional three minutes, a sample of the reaction mass is acidified to a pH of between 1 and 2 and extracted with methylene chloride. The methylene chloride extract sample is washed with water, dried and concentrated on a rotary evaporator. The resulting sample contains 2.2% product by GLC. The reaction mass is continued to be treated with hydrogen sulfide for an additional three hours while warmed to 17°-35° C (25°-35° C for the last hour). The reaction mass is concentrated on a rotary evaporator to 15 ml (a thick yellow slurry). Distilled water (35 ml) and 53 g of 10% NaOH solution is added to the reaction mass and stirred for 20 minutes under a nitrogen blanket at 25°-30° C. The reaction mass is then extracted with two 35 ml portions of methylene chloride and the extracts are combined, dried and concentrated yielding 2.6 g oil.

The basic aqueous solution is acidified with 65 ml aqueous 10% hydrochloric acid to pH=2. The acidified solution is extracted with three 40 ml portions of methylene chloride. The extracts are combined and washed with 30 ml saturated sodium chloride and dried over anhydrous sodium sulfate. The resulting material is gravity filtered and concentrated on a rotary evaporator to yield 6.2 gms of a heavy yellow oil containing 99.3% 2-mercapto-cyclododecanone having the structure:

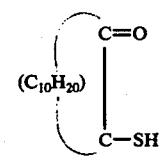

This structure is confirmed by NMR, IR and Mass Spectral analyses of GLC trapped material (8 feet × ¼ inch SE-30 column).

The NMR spectrum is set forth in FIG. 11. The IR spectrum is set forth in FIG. 12.

3.5 gms of material produced according to this example is distilled yielding 2.0 gms of a white solid (M.P. 41°-42° C) at a vapor temperature of 107°-109° C and a vacuum of 0.2 mm Hg. GLC analysis (8 feet × ¼ inch SE-30 column) indicates 99.5% pure 2-mercapto-cyclododecanone.

The NMR analysis is as follows:

| 1.30 ppm (broad singlet) | —CH$_2$— | 14 H |
| --- | --- | --- |
| 1.82 (d) | —SH | ⎫ |
| 3.06–1.65 (m) | —CH$_2$— | ⎬ 7 H |
| 3.62 (triplet of doublets) | O=C—HC—S— | 1 H |

The IR analysis is as follows:
1245 cm$^{-1}$, 1355, 1440, 1470, 1700, 2550, 2860, 2920.
The Mass spectral analysis is as follows:

| m/e | Relative Intensity |
| --- | --- |
| 41 | 84[2] |
| 55 | 100[1] |
| 60 | 70[4] |
| 67 | 44 |
| 69 | 45 |
| 81 | 48 |
| 87 | 83[3] |
| 95 | 36 |
| 98 | 54[5] |
| M214 | 50[6] |

EXAMPLE V

Part (A)

PREPARATION OF 2-CHLORO-3-PENTANONE

Reaction:

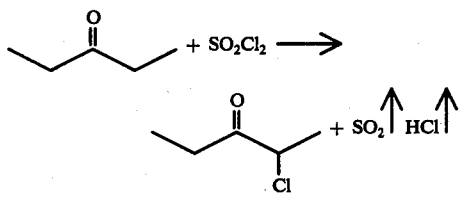

Into a 1000 ml, three-necked, round-bottom flask, equipped with "Y-tube", pot thermometer, 125 ml addition funnel, cold water bath and mechanical stirrer is placed 215 gms (2.5 moles) of diethyl ketone (3-pentanone). Over a period of one hour, 67.5 gms (40 ml; 0.5 moles) of $SO_2Cl_2$ is added, dropwise, from the addition funnel, with stirring, while maintaining the pot temperature at 30°–35° C. At the end of the addition of the $SO_2Cl_2$, water aspirator vacuum is applied with stirring to remove the acidic gases; sulfur dioxide and hydrogen chloride.

Water aspirator vacuum is applied for a period of 2 hours.

GLC analysis (conditions: 8 feet × ¼ inch SE-30 column, 75°–225° C, programmed at 4° C/minute) yields the information that the reaction product is 19.1% 2-chloro-3-pentanone.

The crude material is charged to a 500 ml, three-necked, round-bottom flask, equipped with reflux head, magnetic stirrer, 2.0 × 30 cm distillation column, packed with ⅛ inch helices, heating mantle and pot thermometer. The distillation is carried out at atmospheric pressure and yielding the following fractions:

| Pot Temperature | Vapor Temperature | Weight of Fraction | Percent Chlorinated Product, 2-chloro-3-pentanone by GLC |
|---|---|---|---|
| 112° C | 100° C | 17.7 gms | 0% (only starting material) |
| 120° C | 100° C | 98.0 gms | 0% |
| 134° C | 105° C | 24.2 gms | 0% |
| 135.5° C | 114° C | 6.8 gms | 0% |
| 138° C | 117.5° C | 5.0 gms | 49.1% |
| 139° C | 116.5° C | 4.9 gms | 76.0% |
| 140° C | 122.5° C | 3.3 gms | 85.6% |
| 141.5° C | 122° C | 7.4 gms | 92% |
| 143° C | 123° C | 24.4 gms | 88.5% |

The 92% pure material is used in Part (B), supra.

Part (B)

PREPARATION OF
2-MERCAPTO-3-PENTANONE

Reaction:

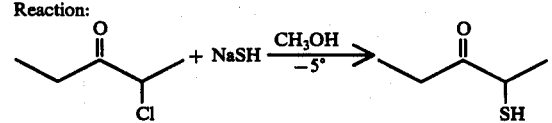

Into a 250 ml, three-necked, round-bottom flask, equipped with magnetic stirrer, pot thermometer, six inch distillation column with gas outlet at top attached to rubber tubing leading above stirring 10% NaOH solution, gas inlet tube for hydrogen sulfide (sub-surface), gas bubbler, isopropyl alcohol/dry-ice bath and 10 ml addition funnel is placed a solution of 7 gms of sodium methoxide in 70 ml anhydrous methanol. While maintaining the reaction mass temperature at between −13° and −9° C, hydrogen sulfide is added thereto over a period of 1.5 hours. While maintaining the reaction mass at a temperature of between −9° and −3° C, the 2-chloro-3-pentanone prepared in Part (A) of this example, is added to the reaction mass over a period of 15 minutes and hydrogen sulfide is continued to be bubbled into the reaction mass for another hour while maintaining the temperature of the reaction mass at between −3° C and +5° C.

GLC analysis (conditions: 8 feet × ¼ inch SE-30 column) of an extracted sample indicates that no chlorinated ketone remains at this point. The reaction mass is then flushed with nitrogen and allowed to warm up to room temperature. The reaction mass is then concentrated on a rotary evaporator using water aspirator vacuum to a volume of 20 ml (yielding a thick white slurry). 55 ml distilled water is then added thereto causing the reaction mass to become a "turbid-yellow" solution. 53 gms of 10% aqueous sodium hydroxide is then added to the reaction mass with stirring while maintaining the temperature at 22°–25° C (pH=10–11). The reaction mass is then extracted with two 50 ml portions of methylene chloride. The remaining basic aqueous solution is then acidified with 65 ml 10% HCl to pH=2 and the resulting acidic solution is extracted with three 50 ml portions of methylene chloride. The methylene chloride extracts are combined and washed with two 30 ml portions of saturated sodium chloride solution. The extracts are then dried over anhydrous sodium sulfate, gravity filtered and concentrated on a rotary evaporator to a weight of 6.0 gms. The desired product, 2-mercapto-3-pentanone is trapped out using preparative GLC (conditions: 8 feet × ¼ inch SE-30 column, operated at 75°–225° C, programmed at 4° per minute).

Mass Spectral, IR and NMR analyses confirm that the resulting product is 2-mercapto-3-pentanone.

The NMR spectrum is set forth in FIG. 13. The IR spectrum is set forth in FIG. 14.

The NMR analysis is as follows:

| | | |
|---|---|---|
| 1.12 ppm (t) | $CH_3-C-C-$ (with C=O) | 3 H |
| 1.48 (d) | $CH_3-C-C=O$ with $S-$ | 3 H |
| 1.86 (d) | $-SH$ | 1 H |
| 2.64 (m) | $-CH_2-C-$ (with C=O) | 2 H |
| 3.48 (m) | $O=C-HC-S-$ | 1 H |

The Mass Spectral analysis is as follows:

| m/e | Relative Intensity |
|---|---|
| 27 | 27[4] |
| 29 | 43[7] |
| 35 | 7 |
| 41 | 7 |
| 45 | 7 |
| 57 | 100[1] |
| 59 | 9.5[6] |
| 60 | 9 |
| 61 | 61[2] |
| M118 | 22[5] |

The infra-red spectrum is set forth in FIG. 14.

The infra-red analysis is as follows:
950 cm⁻¹, 1060, 1130, 1345, 1370, 1405, 1450, 1710, 2550, 2940, 2980.

EXAMPLE VI

GRAPEFRUIT FORMULATION

The following formulation is prepared:

| Ingredients | Parts by Weight |
|---|---|
| Grapefruit oil | 92 |
| Bergamot oil | 2 |
| Citral | 3 |
| Amyl alcohol | 1 |
| Ethyl acetate | 1 |
| 5-Phenyl-4-pentenal | 1 |
| 3-Mercapto-4-heptanol | 0.5 |

When the above grapefruit formulation is added to water at the rate of 1%, an excellent grapefruit drink is prepared. The 3-mercapto-4-heptanol prepared according to Example I gives an intense citrusy note to the instant formulation thereby rendering it more desirable. The effect rendered by the 3-mercapto-4-heptanol can be also rendered by the following materials (individually or in admixture) in the following relative parts by weight:

| Ingredients | Parts by Weight |
|---|---|
| 4-Mercapto-5-nonanone | 1.0 |
| 4-Mercapto-5-nonanol | 1.3 |
| 3-Mercapto-2,6-dimethyl-4-heptanone (also gives strong pleasant desirable buchu leaf oil character) | 0.4 |
| 2-Mercapto-3-pentanone | 1.6 |

EXAMPLE VII

VEGETABLE FLAVOR FORMULATION

2-Mercaptocyclododecanone-1 is added directly to a food product prior to processing and canning. The following illustrates the beneficial flavor effect when 2-mercaptocyclododecanone-1 prepared according to Example IV is added directly to several food products just prior to their consumption:

i. In blended vegetable sauce at approximately 30 ppm: Brings out the green vegetable notes with minty nuances.

ii. In vegetable soup at 40 ppm: Imparts a fresh vegetable flavor. The green notes give the entire vegetable flavor a fuller body.

iii. In bean tomato sauce at approximately 20 ppm: Modifies the flavor by reducing the harsh character of the tomato spice mixture while at the same time adding green fresh notes and developing the "cooked" tomato note to a "fresh" tomato note.

The levels of concentration of the 2-mercaptocyclododecanone-1 may be reduced by 25% when 2-isobutyl thiazole is added at the rate of 5 ppm in addition to the 2-mercaptocyclododecanone-1 to the various products set forth above. It should be understood that noticeable differences in the flavor are discernable at other concentrations.

EXAMPLE VIII

USE OF 2-MERCAPTOCYCLODODECANONE-1 TO ENHANCE THE VEGETABLE FLAVOR OF VEGETARIAN VEGETABLE SOUP

2-Mercaptocyclododecanone-1 is added at the rate of 2 ppm to condensed Vegetarian Vegetable Soup (Shop-Rite²⁰⁰ brand). One liter of water is added to one liter of soup and thoroughly admixed. The resulting mixture is then simmered (200° F) for a period of 10 minutes. The resulting soup is compared by a bench panel with a soup which has no 2-mercaptocyclododecanone-1 added thereto. The soup having the 2-mercaptocyclododecanone-1 added thereto is unanimously preferred as having a more vegetable-like taste with fuller mouthfeel and better aroma, and in addition, pleasant slight minty nuances.

BRIEF DESCRIPTION OF THE DRAWINGS:

FIG. 1 represents the NMR spectrum for 3-mercapto-4-heptanone produced according to Example I (B).

FIG. 2 represents the infra-red spectrum for 3-mercapto-4-heptanone produced according to the process of Example I (B).

FIG. 5 represents the NMR spectrum for 4-mercapto-5-nonanone produced according to Example II (B).

FIG. 6 represents the infra-red spectrum for 4-mercapto-5-nonanone produced according to Example II (B).

Figures 3, 4:
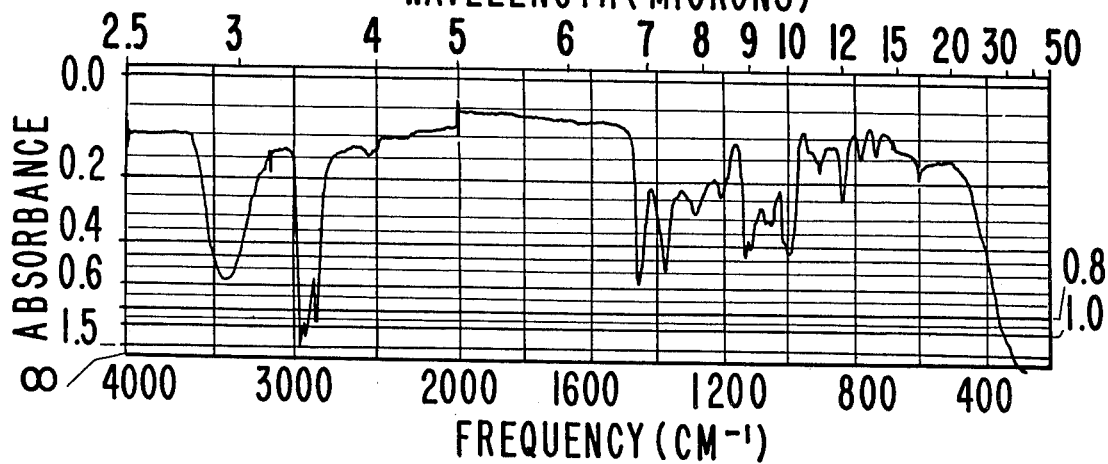
FIG. 3 represents the NMR spectrum for 3-mercapto-4-heptanol produced according to Example I (C).
FIG. 4 represents the infra-red spectrum for 3-mercapto-4-heptanol produced according to Example I (C).
Figure 7:
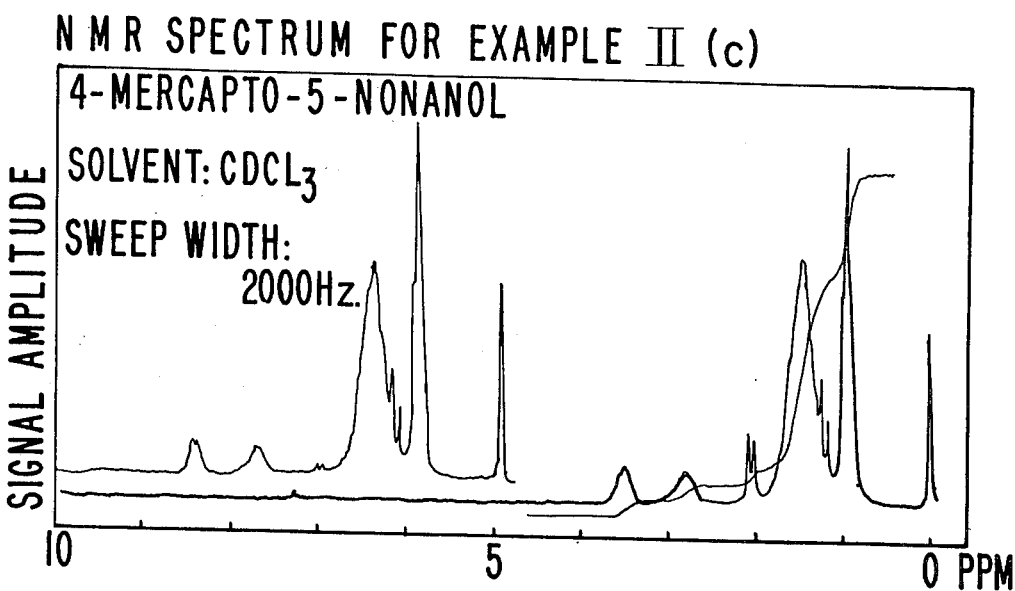
FIG. 7 represents the NMR spectrum for 4-mercapto-5-nonanol produced according to Example II (C).
Figure 8:
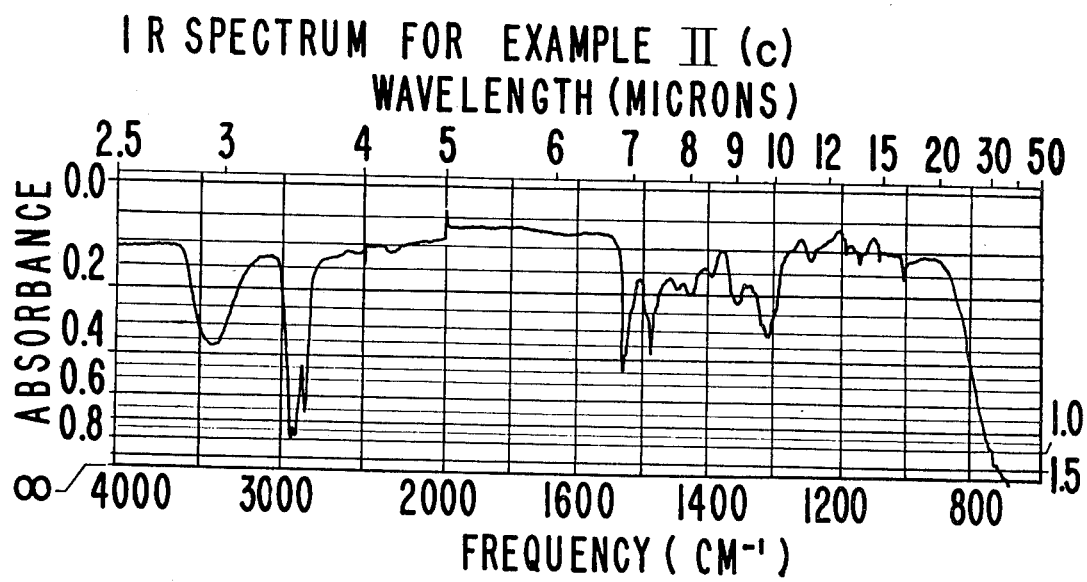
FIG. 8 represents the infra-red spectrum for 4-mercapto-5-nonanol produced according to Example II (C).
Figure 9:
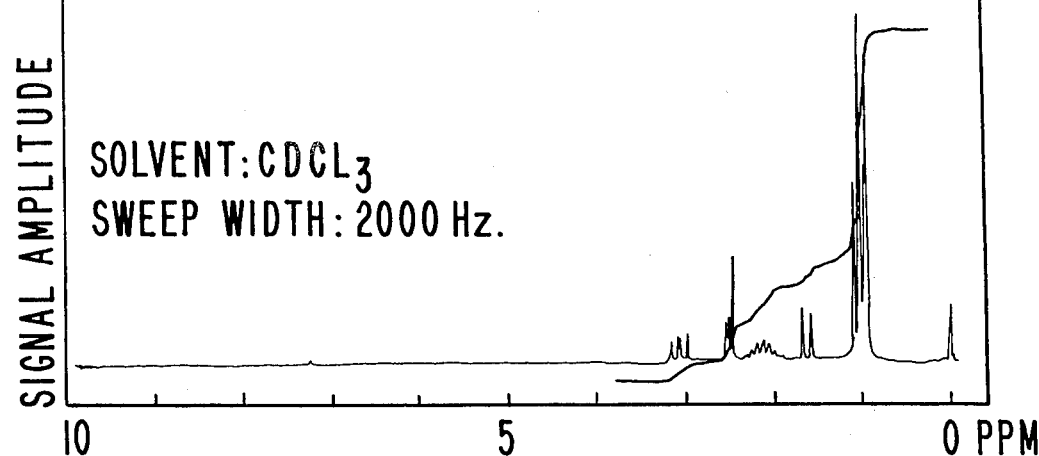
FIG. 9 represents the NMR spectrum for 2,6-dimethyl-3-mercapto-heptanone-4 produced according to Example IV (B).
Figure 10:
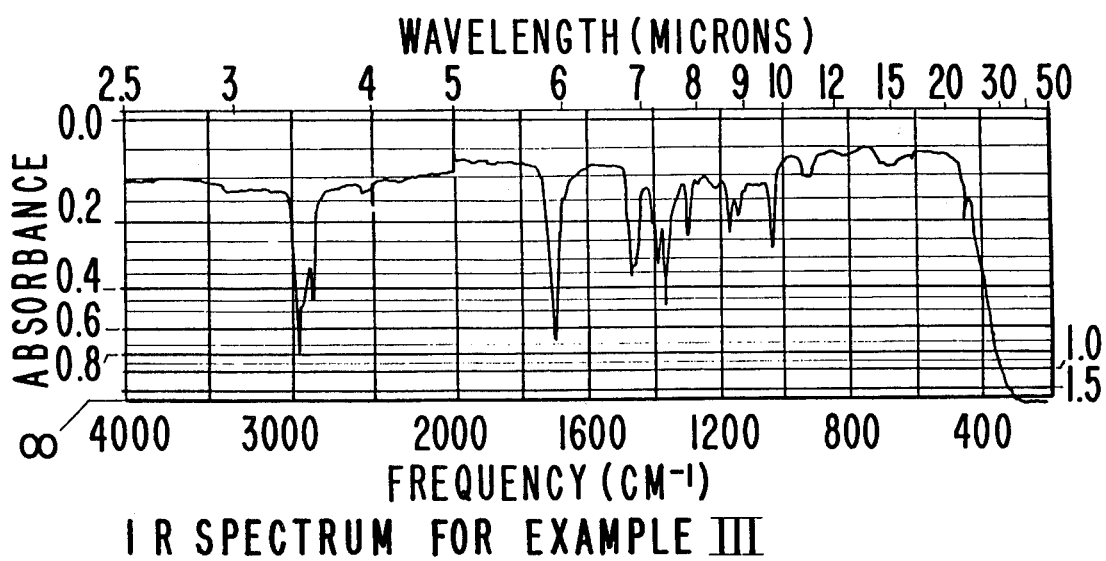
FIG. 10 represents the infra-red spectrum for 2,6-dimethyl-3-mercapto-heptanone-4 produced according to Example IV (B).
Figure 11:
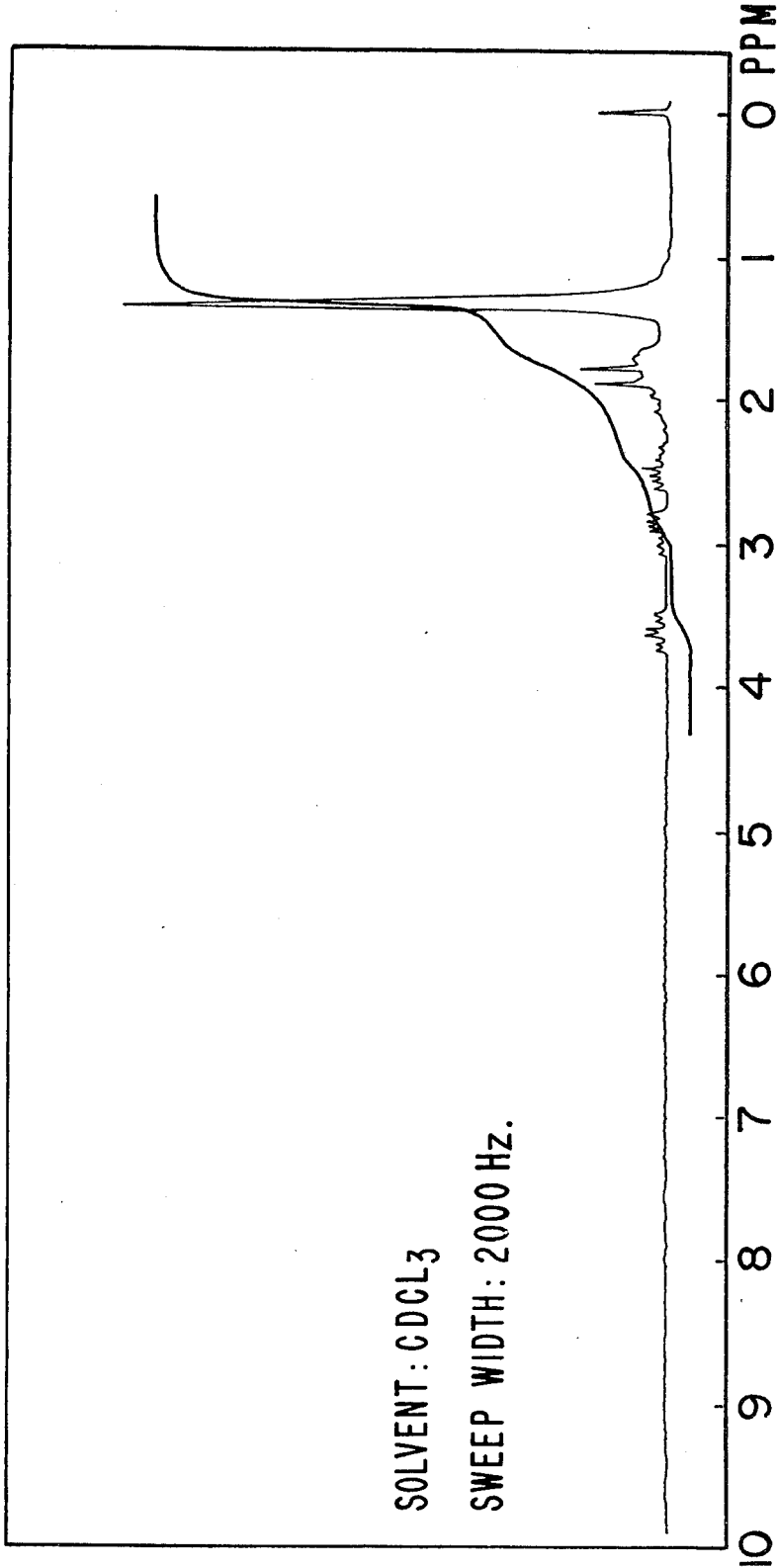
FIG. 11 represents the NMR spectrum for 2-mercaptocyclododecanone-1 produced according to Example IV.
Figure 12:
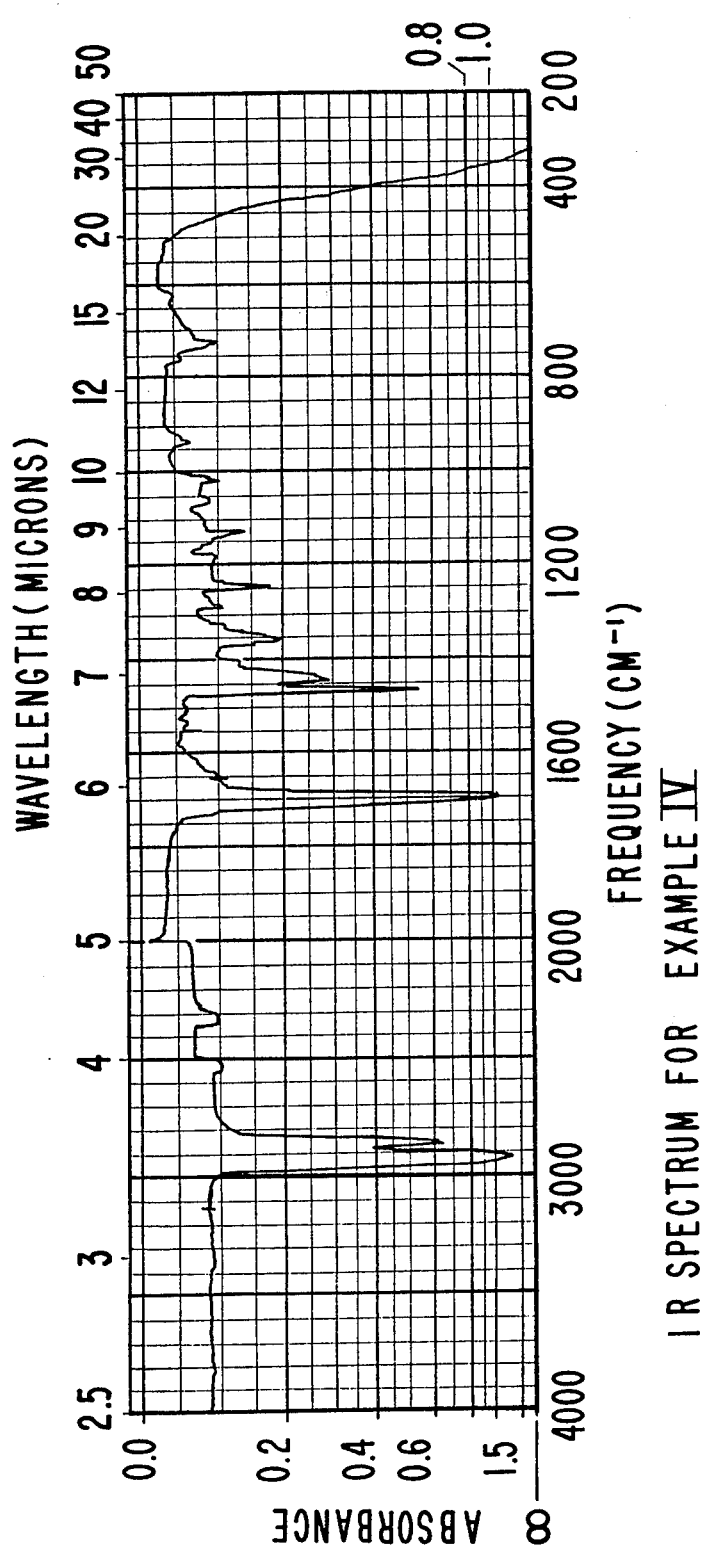
FIG. 12 represents the infra-red spectrum for 2-mercaptocyclododecanone-1 produced according to Example IV.
Figure 13:
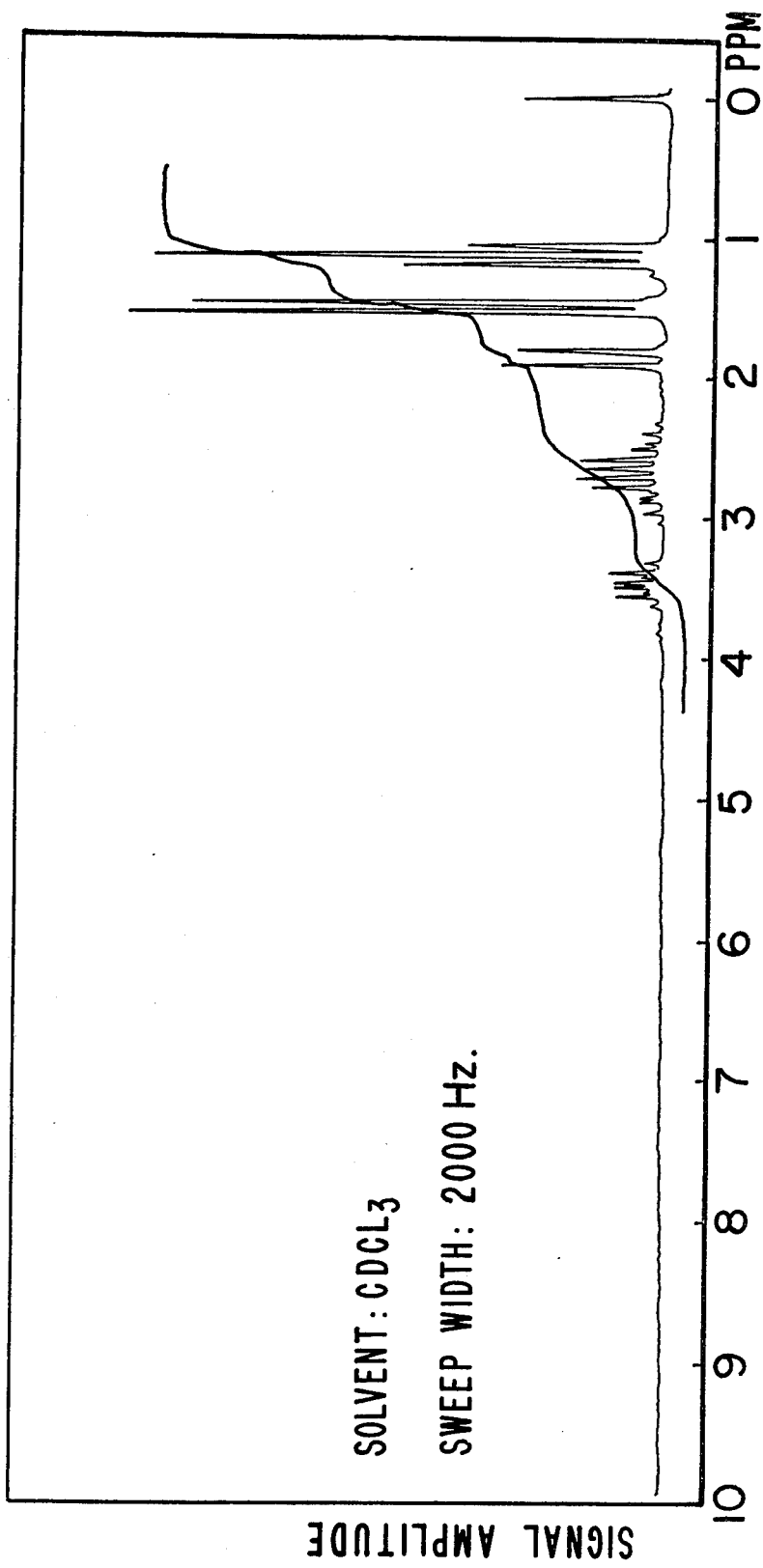
FIG. 13 represents the NMR spectrum for 2-mercapto-3-pentanone produced according to Example V.
Figure 14:
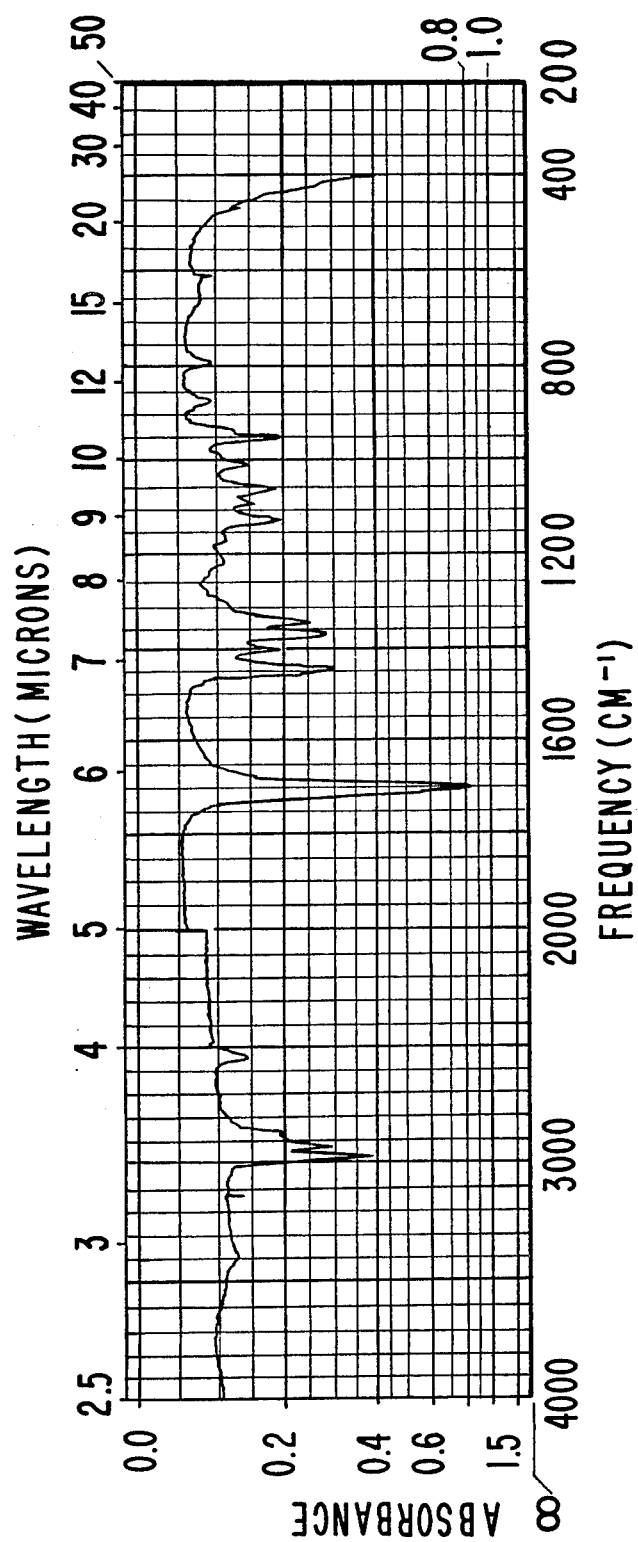
FIG. 14 represents the infra-red spectrum for 2-mercapto-3-pentanone produced according to Example V.

What is claimed is:

1. A process for augmenting or enhancing the fruity or vegetable aroma or taste of a foodstuff which comprises adding thereto from about 0.02 ppm up to about 50 ppm by weight of said foodstuff of a sulfur-containing compound which is 3-mercapto-4-heptanol.

2. A process for augmenting or enhancing the fruity or vegetable aroma or taste of a foodstuff which comprises adding thereto from about 0.02 ppm up to about 50 ppm by weight of said foodstuff of a sulfur-containing compound which is 4-mercapto-5-nonanol.

3. A composition for augmenting or enhancing the fruity or vegetable flavor of a foodstuff comprising (i) from 0.05% up to 5% by weight of said flavor of 3-mercapto-4-heptanol, the remainder of said composition being (ii) at least one adjuvant selected from the group consisting of:
grapefruit oil;
bergamot oil;
citral;
amyl alcohol;
ethyl acetate;
5-phenyl-4-pentenal;
5-phenyl-2-pentenal;
limonene;
n-octanal;
n-decanal;
geraniol;
cadinene;
dimethylanthranilate;
vanillin;
amyl butyrate;
2-(n-pentyl)thiazole;
2-(i-butyl)thiazole;
2-(i-propyl)thiazole;
2-(n-propyl)thiazole;
The dimethyl acetal of 2-phenyl-4-pentenal;
methional;
4-methylthiobutanal;
2-ethyl-3-acetyl pyrazine;
tetramethyl pyrazine;
2-methyl pyrazine;
2-trans hexenal;
maltol;
2-phenyl-4-pentenal;
2-phenyl-4-pentenal dimethyl acetal; and
2-phenyl-4-pentenal diethyl acetal.

4. A composition for augmenting or enhancing the fruity or vegetable flavor of a foodstuff comprising (i) from 0.05% up to 5% by weight of said flavor of 4-mercapto-5-nonanol, the remainder of said composition being
ii. at least one adjuvant selected from the group consisting of:
grapefruit oil;
bergamot oil;
citral;
amyl alcohol;
ethyl acetate;
5-phenyl-4-pentenal;
5-phenyl-2-pentenal;
limonene;
n-octanal;
n-decanal;
geraniol;
cadinene;
dimethylanthranilate;
vanillin;
amyl butyrate;
2-(n-pentyl)thiazole;
2-(i-butyl)thiazole;
2-(i-propyl)thiazole;
2-(n-propyl)thiazole;
The dimethyl acetal of 2-phenyl-4-pentenal;
methional;
4-methylthiobutanal;
2-ethyl-3-acetyl pyrazine;
tetramethyl pyrazine;
2-methyl pyrazine;
2-trans hexenal;
maltol;
2-phenyl-4-pentenal;
2-phenyl-4-pentenal dimethyl acetal; and
2-phenyl-4-pentenal diethyl acetal.

* * * * *